United States Patent [19]

Greneker

[11] 4,177,698
[45] Dec. 11, 1979

[54] FINGER FIT IMPLEMENT
[76] Inventor: Lillian L. Greneker, 321 E. 69th St., Apt. 1E, New York, N.Y. 10021
[21] Appl. No.: 889,735
[22] Filed: Mar. 24, 1978
[51] Int. Cl.² .................................................. B25B 9/00
[52] U.S. Cl. ................................... 81/1 R; 81/177 C; 30/298
[58] Field of Search ...................... 81/1 R, 43, 177 C; 294/25; 30/298

[56] References Cited
U.S. PATENT DOCUMENTS 1,000,226  8/1911  Arwine ........................ 81/177 C UX
2,151,846  3/1939  Greneker ................................ 81/1 R
3,293,958  12/1966  Smith ........................................ 81/43

Primary Examiner—James G. Smith
Attorney, Agent, or Firm—Daniel M. Rosen

[57] ABSTRACT

A finger fit implement comprising a shaped hollow member having an opening at one end to accommodate the entry of a finger and an opposed off centered tapered internal end to be mated against the tip and nail portion of said finger. The opposed end portion having an external fitting means for attachment of various tool elements.

7 Claims, 7 Drawing Figures

U.S. Patent  Dec. 11, 1979  4,177,698
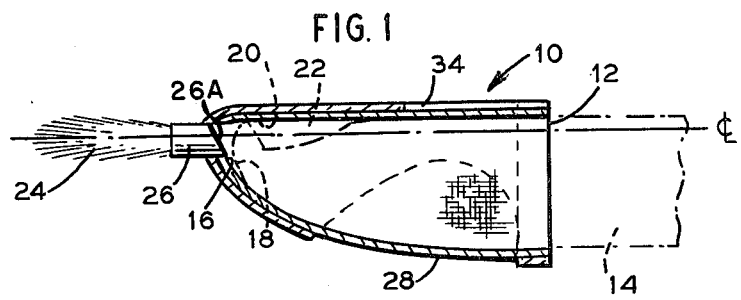
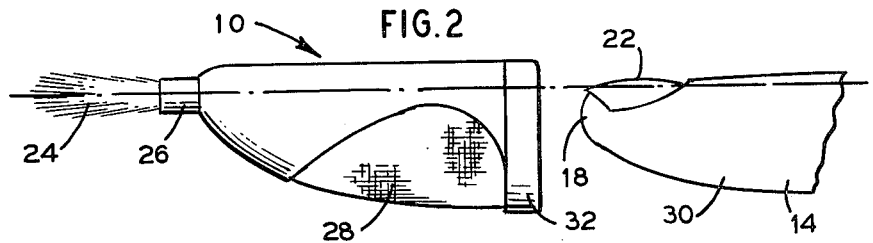
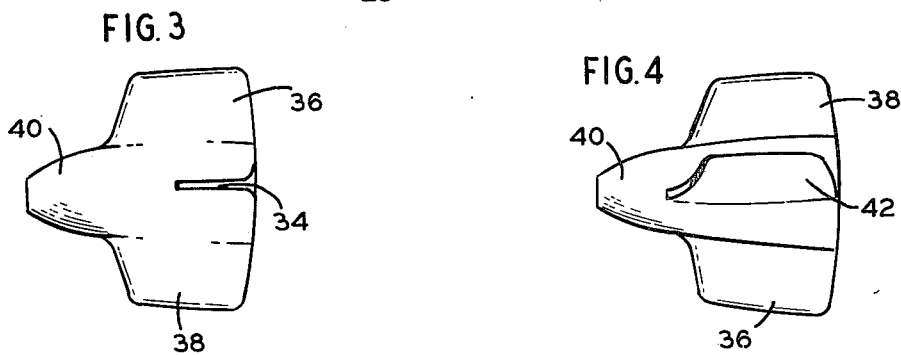
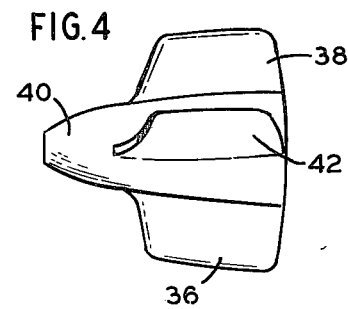
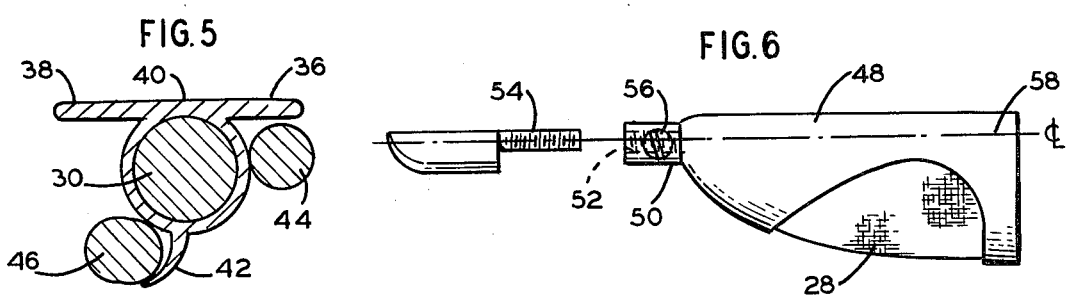
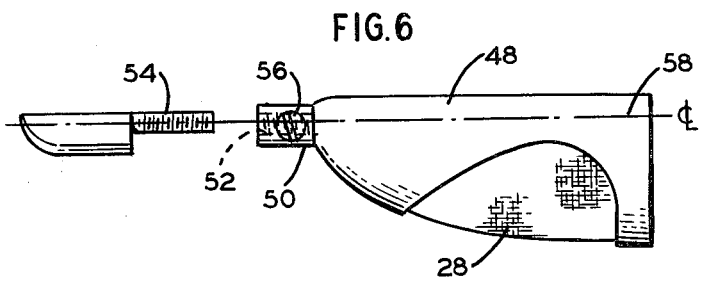
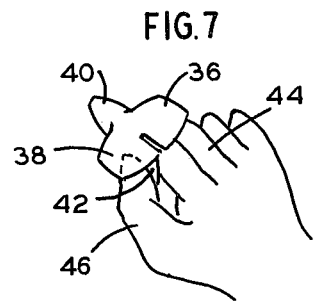

FINGER FIT IMPLEMENT

FIELD OF THE INVENTION

This invention relates generally to detachable finger implements and more particularly to an improved finger fit implement adapted to have mounted thereon one or a plurality of interchangeable elements adaptable for finger manipulation.

BACKGROUND AND SUMMARY OF THE INVENTION

Many devices have been proposed or on the market which assists in the protection of the fingers are engaged in the manipulation of objects and devices. These devices, such as thimbles and other types of finger protectors all share in common a difficulty in operation in that they are never precisely fittable with respect to an individual finger. As results of this imprecise fitting, manipulation becomes extremely difficult and the main function of such devices is thus limited to areas such as protection, as in the common thimble.

In certain prior finger fit implements, it was discovered that it is desirable to provide a device which can manipulate a tool by means of a finger fit implement. In my prior U.S. Pat. No., 2,151,846, I have described such an implement. In my patent however the implement is symmetrical about its common axis with a tapering profile approaching a point on the central axis. As a result, the implement does not precisely fit with respect to the finger and the finger manipulation becomes imprecise. Other patents have also proposed the use of finger implement devices, such as U.S. Pat. Nos. 2,418,638, and 1,473,953. Both of these patents however have merely used standard variations of fingertip shields and do not provide any recognition of the solution of the imprecise fit problem caused by the mismatch between device and fingertip. Other patents showing finger shields such as 6,179,929, 1,160,522 and 1,257,846, all suffer from similar drawbacks.

It is therefore the principle object of the present invention to provide an improved finger fit implement which will provide greater security between finger and implement as a result of the improved configuration of the internal profile thereof.

It is a further object of the present invention to provide a finger implement with a more secure fit relative to the finger employed for manipulation.

It is another object of the present invention to provide appropriate structural configurations to the finger fit implement which will enable it to be capable of greater digital manipulation during the course of operation.

The foregoing objects are achieved in accordance with the present invention by providing the finger fit implement as a shaped hollow member having an opening at one end for accommodating the entry of a finger, and an opposed off centered tapered internal end portion shaped so as to be mated against and supported by the tip and nail portion of the inserted finger. The opposed end portion is also provided with an external fitting for accommodating an implement for manipulation by the finger.

The foregoing summary of the present invention will become more apparent from the following more detailed description and the pending drawings.

BRIEF DESCRIPTION OF THE DRAWINGS

FIG. 1 shows a cross sectional view of the finger implement of the present invention illustrating the position of the finger inserted therein.

FIG. 2 is a schematic illustration of a typical finger fit implement of the present invention in a perspective view, and showing its relationship to a finger.

FIG. 3 is a top view of the present invention.

FIGS. 4–6 show a further alternative embodiment of the present invention showing the relative relationship between several fingers and the manipulators attached to the implement, and FIG. 7 shows a detail of the external fitting means of the implement wherein a plurality of elements may be interchangeable.

DETAILED DESCRIPTION OF THE PREFERRED EMBODIMENT

Referring now to FIGS. 1–2, the cross sectional of a finger fit implement in accordance with the present invention is shown. As is evident, the implement 10 is provided with an opening 12 at one end designed to accommodate the entry of a finger. The opposed end 14 is provided with an off centered tapered internal portion 16 which is designed to match the general configuration of the external shape of the end portion 18 of a fingertip. The inner surface 16 mates against the end portion 18 of the finger and thereby provides firm and rigid support as well as good fit between the two mating surfaces. The off centered tapered portion 16 includes a further recess portion 20 which may be employed for accommodating a fingernail 22 which may extend into the recess 20 to some length.

The external shape of the implement 10 may conform somewhat to the internal configuration of the implement as shown in FIG. 1. An element 24 is attached as holding means such as to the external tip 26 of the implement 10 for manipulation by the finger. The tip 26 is provided with a bevelled inner surface 26A so as to provide greater mating with the fingertip. Active perception by the finger, a property physiologically termed proprioceptive may be increased by the insertion of a relatively thin material 28 in the area normally accommodated at the sensitive portion of the finger 30. This thinner material, which may be silk or some other form of material, or in fact may be an opening without material at all, is designed to engage and lie flat along the surface of the fingertip 30 to the extent possible.

The material of which the main structure of the element 10 is constructed can be any form of rigid or relatively stiff material such as paper, metal, leather or plastic. The implement 24 may be attached at the point 26 by any simple means such as adhesive, clamp, threaded bushing or the like.

For maintaining the implement securely to the finger, the end portion adjacent to the open end of the implement may include some suitable securing means such as a cuff 32 of elastic or the like. Alternatively, the upper portion of the implement 10 may be slit, with the remaining material of the implement being relatively elastic so that the penetration therein of a finger causes slight expansion along the slit and provides a relatively tight compressive fit about the end of the finger. Such a slit is shown as element 34 in FIG. 3. FIG. 3 shows the top of the implement of the present invention wherein a plurality of manipulative members 36 and 38 are formed or attached to the member 40 so as to provide increased finger manipulation. As shown in FIG. 5, which represents a right end view of the element of FIG. 3, a further optional manipulative element 42 may be added. In this configuration, the index finger is presumed to be the finger entering the implement 40, thereby permitting the right manipulative wing 36 to be manipulated by the forefinger 44, and the lower manipulative wing 42 manipulated by the thumb 46. The thumb is also moveable so that it may be employed to manipulate the upper wing 38, thereby giving bi-directional rotatable movement to the implement 40. This is shown in perspective detail in FIGS. 5 and 6 wherein the relative position of the manipulative wings is illustrated with respect to the various manipulative fingers, same reference numerals being employed to indicate commonality between figures.

Referring now to FIG. 7, the implement 48 is shown in detail wherein the tip portion 50 consists of a ferrule having an enternally threaded portion 52 designed to mate with a correspondingly threaded element 54. The element 54 is shown as a scapel which may be employed by a physician by manipulation of the fingertip tool for surgical procedures. It will be obvious however that the element 54 can be any tool employed for digital manipulation, such as a paint brush, writing implements, screwdriver or other type of fingertip tool. Attachment of the tool or element 54 to the ferrule or bushing 50 may be accomplished by the mating thread portions or by an appropriate set screw 56 accommodated in the bushing, or may be friction fit or be any other secure means of attachment.

Summarizing the inventive aspect of the improvement in this case, it will be evident that I have found that an improved finger fit manipulative implement may be designed by appropriately mating the internal support surface of the implement to the fingertip of the user. This is done by off centering and tapering the internal portion of the mating end of the implement, and providing a relatively linear surface along the longitudinal axis corresponding to the upper portion of the finger, with the manipulative element secured along this axis. This is best illustrated in FIG. 7, although it will be evident from all of the other figures as well, that the longitudinal axis 58 represents both the longest extending dimension of the finger, as well as the strongest portion of the finger running through the fingernail, and terminates in the means which are employed to affix the element to the implement. It is this essential and principle characteristic which provides greater manipulatability as well as security of operation to the implement as described by the present invention.

In addition, the implement may take other configurations such as a shorter body, or a longer body, completely enclosed or partially enclosed, or other desired shape, as long as the off center axial alignment of the manipulative element with the upper longitudinal dimension of the manipulating finger is maintained.

Other uses, variations and structural modifications of the present improvement will be evident to those skilled in the art.

I claim:

1. A finger fit implement comprising a shaped hollow member, one end of which forming an opening to accomodate the entry of a finger, and having an interior shape including a top portion generally parallel to the axis of said member and a lower portion off centered and tapered with respect to said axis of said member and joining said top portion forming a closed end of said member; an external fitting means for accomodating an element for manipulation by said finger, said fitting means positioned in axial alignment with said top portion of said opening and secured to said member at the point where said top portion and said tapered lower portion join, said fitting including a bevelled inner surface generally parallel to said tapered lower portion of said member providing a conforming fit on said finger thus increasing manipulability and fit, a plurality of rigid segments positioned at circumferentially spaced positions about said hollow shaped member, said segments digitally engageable for manipulation support of said member, and providing the area of said implement about the central portion of the finger of relatively thin material so as to be transmissive of pressure and thereby provide an area for increased touch sensitivity.

2. The implement of claim 1, wherein said segments are a pair directly opposed about said member.

3. The implement of claim 1, wherein said segments include a pair directly opposed about said member, and a third circumferentially therebetween said pair.

4. The implement of claim 1, wherein said member is secured to said finger by a relatively elastic shaped ring shaped portion surrounding the open end.

5. The implement of claim 1, wherein said member is secured to said finger by a slit in the open end thereof, the sides of said slit separating upon entry by said finger to apply a compressive stress about said finger.

6. The implement of claim 1, wherein said fitting means is a ferrule mounted along the longitudinal axis of said implement and adaptable for universal mounting therein of a plurality of interchangeable elements.

7. The implement of claim 6, wherein said ferrule is threaded for mating with a correspondingly threaded mating component.

* * * * *